US006214887B1

(12) United States Patent
Côté et al.

(10) Patent No.: US 6,214,887 B1
(45) Date of Patent: Apr. 10, 2001

(54) VASCULAR REMODELING AGENT (75) Inventors: Gilles Côté, Ile-Des-Soeurs; Jean-Claude Tardif, Laval, both of (CA)

(73) Assignee: Quatro Scientific, Inc., Montreal (CA)

( * ) Notice: Subject to any disclaimer, the term of this patent is extended or adjusted under 35 U.S.C. 154(b) by 0 days.

(21) Appl. No.: 09/142,507

(22) PCT Filed: Mar. 23, 1998

(86) PCT No.: PCT/CA98/00269

§ 371 Date: Sep. 8, 1998

§ 102(e) Date: Sep. 8, 1998

(87) PCT Pub. No.: WO98/42327

PCT Pub. Date: Oct. 1, 1998

Related U.S. Application Data (60) Provisional application No. 60/041,456, filed on Mar. 24, 1997.

(51) Int. Cl.$^7$ .................................................... A61K 31/10
(52) U.S. Cl. .............................................................. 514/712
(58) Field of Search .............................................. 574/712

(56) References Cited

U.S. PATENT DOCUMENTS 5,439,446 * 8/1995 Barry ........................................ 604/96

FOREIGN PATENT DOCUMENTS

| 0 254272 | 1/1988 | (EP) . |
| WO 93 09762 | 5/1993 | (WO) . |
| WO 97 13501 | 4/1997 | (WO) . |

OTHER PUBLICATIONS

New England Journal of Medicine, vol. 330, No. 14, Apr. 7, 1994, pp. 981–993, Landau, et al.
Proc. Natl. Adac. Sci. USA, 1992, vol. 89, pp. 11312, 11316, Ferns, et al.
Circulation, vol. 88, No. 2, Aug. 1993, pp. 628–637, Schneider, et al.
J. Clin. Invest., vol. 91, Apr. 1993, pp. 1282–1288, Freyschuss, et al.
Arteriosclerosis, Thrombosis, and Vascular Biology, vol. 15, No. 1, Jan. 1995, pp. 156–165, Nunes, et al.
Circulation, vol. 86, Nov. 1990, p. II–299, Abstract No. 1189, Lee, et al.
Clinical Therapeutics, vol. 15, No. 2, 1993, pp. 374–382, Setsuda, et al.
American Heart Journal, vol. 132, No. 1, Part 1, Jul. 1996, pp. 23–29, Watanabe, et al.
Journal of the American College of Cardiology, Abstracts–Poster, Abstract No. 1031–28, Feb. 1996, p. 391A, Yokoi, et al.
Journal of the American College of Nutrition, vol. 11, No. 1, pp. 68–73 (1992), Demaio, et al.
International Journal of Cardiac Imaging, 8:165–173, 1992, Lesperance, et al.
American Journal of Cardiology, vol. 64, Sep. 1, 1989, pp. 462–465, Lesperance, et al.
New England Journal of Medicine, 318:1714–1719, Jun. 30, 1988, Schwartz, et al.
American Journal of Cardiology, vol. 77, Mar. 15, 1996, pp. 649–652, O'Keefe, et al.
Arteriosclerosis and Thrombosis, vol. 12, No. 3, Mar. 1992, pp. 318–324, Reaven, et al.
Mayo Clin. Proc., 63:390–408, 1988, Southorn, et al.
Nature, vol. 344, pp. 160–162, Mar. 8, 1990, Kugiyama, et al.
New England Journal of Medicine, vol. 320, No. 14, pp. 915–924, Apr. 6, 1989, Steinberg, et al.
Circulation Research, vol. 75, No. 4, pp. 650–658, Oct. 1994, Strauss, et al.

(List continued on next page.)

*Primary Examiner*—James H. Reamer
(74) *Attorney, Agent, or Firm*—Smith Gambrell & Russell, LLP (57) ABSTRACT

Probucol exerts a positive effect on vascular remodeling. By using probucol to promote vascular remodeling by the method of the invention, favorable results can be obtained in treating such diseases and conditions as restenosis following transluminal coronary angioplasty, intimal smooth muscle cell hyperplasia, vascular occlusion, or restenosis following transluminal angioplasty or atherectomy procedures performed on the coronary, iliac, femoral, renal or carotid arteries. This effect was determined based upon an IVUS substudy from the MVP trial. Beginning 30 days before PTCA, 317 patients were randomly assigned to receive either probucol, multivitamins, the combination of drugs, or placebo. Patients were then treated for six months after PTCA. 96 patients (111 segments) underwent IVUS examination immediately after angioplasty and at follow-up. The anatomic cross-section selected for serial analysis was the one at the angioplasty site with the smallest lumen area at follow-up. Quantitative analysis consisted in measurements of lumen area and the area within the external elastic membrane (EEM). Wall area was calculated as the difference between EEM and lumen areas. Results. In the placebo group, lumen area at follow-up decreased by −1.21±1.88 mm$^2$, and wall and EEM areas increased by 1.50±2.50 mm$^2$ and 0.29±2.93 mm$^2$. The change in lumen area correlated more strongly, however, with the change in EEM area (r=0.53, p=0.002) than with the change in wall area (r=−0.13, p=0.49). Lumen loss was −1.21±1.88 mm$^2$ in the placebo group, −0.83±1.22 mm$^2$ for vitamins alone, −0.25±1.17 mm$^2$ for combined treatment and −0.15±1.70 mm$^2$ for probucol alone (p=0.002 for probucol versus no probucol and p=0.85 for vitamins versus no vitamins). The change in wall area was similar in all groups. EEM area increased at follow-up by 0.29±2.93 mm$^2$ in the placebo group, 0.09±2.33 mm$^2$ for vitamins only, 1.17±1.61 mm$^2$ for combined treatment and 1.74±1.80 mm$^2$ for probucol only (p=0.006 for probucol versus no probucol).

16 Claims, 4 Drawing Sheets

OTHER PUBLICATIONS

Science, vol. 231, pp. 405–407, Jan. 24, 1986, Langille, et al.
American Journal of Cardiology, vol. 57, pp. 16H–21H, Jun. 27, 1986, Steinberg, et al.
New England Journal of Medicine, vol. 332., No. 8, pp. 488–493, Feb. 23, 1995, Anderson, et al.
J. Clin. Invest., vol. 77, Feb. 1986, pp. 641–644, Parthasarathy, et al.
New England Journal of Medicine, vol. 331, No. 20, pp. 1331–1337, Weintraub, et al.
American Journal of Cardiology, 1988, 62:77B–81B, Ku, et al.
Circulation Research, vol. 75, No. 1, Jul. 1994, pp. 181–189, Galis, et al.
Journal of Lipid Research, vol. 33, 1992, pp. 899–906, Jialal, et al.
Annals New York Academy of Sciences, 570:7–22, 1989, Burton, et al.
Journal of Surgical Research, 40:519–527, 1986, Cavarocchi, et al.
Journal of Lipid Research, vol. 33, 1992, pp. 385–397, Kagan, et al.
Faseb Journal, vol. 6, Apr. 1992, pp. 2440–2448, Reiser, et al.
Journal of Lipid Research, vol. 33, 1992, pp. 131–137, Elinder, et al.
Biochemistry, vol. 35, No. 40, 1996, pp. 13011–13020, Tsujita, et al.
Journal of the Canadian Dietetic Association, vol. 54, No. 4, Winter 1993, pp. 185–189, Robichon–Hunt, et al.
Journal of the Canadian Dietetic Association, vol. 57, No. 1, Spring 1996, pp. 7–11, Beaudry, et al.
Chemical Abstracts, vol. 120, No. 13, Mar. 28, 1994, Columbus, Ohio, USA; Abstract No. 153345, xp002076406, see abstract & Circulation, vol. 88, No. 2, 1993, pp. 628–637, Schneider, et al.
Chemical Abstracts, vol. 124, No. 9, Feb. 26, 1996, Columbus, Ohio, USA; abstract No. 105978, XP 002076407, see abstract & Domyaku Koka, vol. 23, No. 1/2, 1995, pp. 71–80, Miyauchi, et al.
Chemical Abstracts, vol. 125, No. 11, Sep. 9, 1996, Columbus, Ohio, USA; abstract No. 132303, XP002076408, cited in the application, see abstract & American Heart Journal, vol. 132, No. 1, 1996, pp. 23–29, Watanabe, et al.
Chemical Abstracts, vol. 125, No. 23, Dec. 2, 1996, Columbus, Ohio, USA, abstract No. 292744, XP002076409, cited in the application, see abstract & Jpn.Heart J. vol. 37, No. 3, 1996, pp. 327–332, Lee, et al.
Chemical Abstracts, vol. 127, No. 14, Oct. 6, 1997, Columbus, Ohio, USA, abstract No. 185634, XP002076410, cited in the application, see abstract & New England Journal of Medicine, vol. 337, No. 6, 1997, pp. 365–372, Tardiff, et al.
Chemical Abstracts, vol. 127, No. 23, Dec. 8, 1997, Columbus, Ohio, USA, abstract No. 314581, XP002076411, cited in the application, see abstract & J. Am. Coll. Cardiol., vol. 30, No. 4, 1997, pp. 855–862, Yokoi, et al.
Chemical Abstracts, vol. 128, No. 19, May 11, 1998, Columbus, Ohio, USA; abstract No. 225987, XP0002076412, see abstract & Circulation, vol. 97, No. 5, 1998, pp. 429–436, Rodes, et al.

* cited by examiner

VASCULAR REMODELING AGENT

This application was filed as the international application, PCT/CA98/00269 on Mar. 23, 1998, which is a continuation of U.S. Provisional Application No. 60/041,456 filed Mar. 24, 1997.

INTRODUCTION AND BACKGROUND

Restenosis post-coronary dilation is a common disease of iatrogenic etiology that occurs as a direct consequence of arterial injury induced at the time of angioplasty. In the United States, over 500,000 coronary angioplasty procedures are performed annually and this number has been increasing steadily. Despite technical advances and multiple pharmacologic interventions, most studies have found that the incidence of angiographic restenosis remains in the range of 40%. The presenting symptom in the majority of patients with restenosis is exertional angina. Although clinical evidence for restenosis (MI, coronary revascularization, or recurrent angina) may vary from one study to another, clinical restenosis is generally seen in 25 to 35% of the patients within 6 months of their procedure (Circulation 1992; 86:100–110). Restenosis is a time-limited event. Serial angiographic follow-ups have shown that restenosis is most prevalent between 1 and 4 months and rarely occurs beyond 6 months after coronary angioplasty (*J Am Coll Cardiol* 1988; 12:616–23). The most common treatment strategy for restenosis is repeat angioplasty.

In the past decade, research on prevention of restenosis with pharmacological agents has been almost uniformly disappointing, except for some positive findings with a few drugs yielding conflicting results. The classes of agents tested in a placebo-controlled, randomized study have included antithrombotic agents, fish oil, calcium channel blockers, angiotensin-converting enzyme inhibitors, lipid-lowering agents, steroids, other antiproliferative agents, and magnesium.

Several studies have examined the efficacy of other methods of percutaneous revascularization in the prevention or the treatment of coronary restenosis. Such modalities include: directional and rotational atherectomy, excimer laser-assisted angioplasty, cutting-balloon angioplasty, heat-generating angioplasty devices and coronary stenting.

Other than coronary stenting, no other percutaneous revascularization procedure offers demonstrated advantage over conventional PTCA in preventing or limiting recurring restenosis. Although stent implantation may, in some patients (de novo lesion, native coronary artery with a reference diameter larger than 3.0 mm) prove beneficial (*N Engl J Med* 1994; 331:489–495) (*N Engl J Med* 1994; 331:496–501), its clinical or angiographic superiority in vessels smaller than 3.0 mm in diameter has never been shown (*Semin Intervent Cardiol* 1996; 1:255–262).

Our understanding of the pathophysiology of restenosis has been steadily improving. Once believed to be initiated by an early thrombotic phenomenon, restenosis has been considered in the past 7 years essentially a proliferative process taking place in the weeks following angioplasty at the site of arterial injury. Cytologic analyses of post mortem and atherectomy samples have revealed that smooth muscle cells are the predominant cells responsible for this hyperplastic response. One possible explanation for the negative results with the pharmacologic studies aimed at reducing neointimal hyperplasia is that these strategies targeted the wrong mechanism.

More recently, animal and clinical studies have begun to question the predominant role of cellular proliferation in restenosis and indicate that arterial remodeling is, in fact, an important aspect of the restenosis process (*Circulation* 1994; 89:2809–15). Inadequate vascular remodeling has been described not only after coronary balloon angioplasty but also after directional and rotational atherectomy and laser angioplasty (*Circulation* 1996; 94:35–43). Arterial remodeling is defined as a change in total arterial or external elastic membrane (EEM) cross-sectional area (CSA) over time. Arterial remodeling can be bi-directional. Adaptive positive arterial remodeling (an increase in arterial CSA) may represent a compensatory response of blood vessels to hemodynamic stress, arterial injury, and cellular proliferation. Adaptive arterial remodeling has first been described in early coronary artery atherosclerotic disease process (*N Engl J Med* 1987; 316:1371–5). Adaptive positive arterial remodeling in non-instrumented arteries prevents the reduction in lumen dimensions until plaque occupies 20% to 40% of the CSA within the internal elastic membrane (20% to 40% cross-sectional narrowing or plaque burden) (*Am J Cardiol* 1997; 80:1408–13). Alternatively, pathologic negative arterial remodeling (a decrease in arterial CSA or chronic arterial constriction) has been shown to contribute to lumen compromise in chronic, focal de novo stenosis in femoral and coronary arteries (*Circulation* 1995; 91:1444–9 and *Circulation* 1997; 95:1791–8).

SUMMARY OF THE INVENTION

This invention concerns methods and devices for promoting vascular remodeling. By the invention, vascular remodeling is accomplished by the systemic or local administration of the drug, probucol; 4,4'-([1-methylethylidene)bis(thio)]bis-[2,6-bis(1,1-dimethylethyl)phenol]. The preparation of probucol has been described in U.S. Pat. No. 3,576,883 and its use as a cholesterol-lowering agent has also been described in U.S. Pat. No. 3,862,332. Its use to inhibit angiographic and clinical restenosis, i.e., death from cardiac cause, acute myocardial infarction, recurrence or exacerbation of angina pectoris and the need for revascularization (coronary bypass surgery or re-angioplasty) post-coronary angioplasty by promoting positive vascular remodeling has not previously been described. By using probucol to promote vascular remodeling by the method of the invention, favorable results can be obtained in treating diseases and conditions such as restenosis following balloon angioplasty, directional or rotational atherectomy, laser angioplasty and post-stent implantation. Promoting positive vascular remodeling would be favorable not only for interventions performed in the coronary arteries but also when these procedures are performed in any vascular structure, i.e., peripheral vessels (iliac, femoral etc.), renal, mesenteric, or carotid arteries, etc. Furthermore, promoting positive vascular remodeling would be favorable in the long-term treatment of patients with ischemic syndromes as seen in coronary artery disease, peripheral vascular disease, mesenteric vascular disease, cerebro-vascular disease, etc. The benefit of a positive vascular remodeling agent would also be desirable for the treatment of conditions such as chronic arterial hypertension, post-heart transplant, post-bypass surgery, etc.

Five small clinical studies have suggested that probucol started before angioplasty may prevent restenosis (*Circulation* 1991; 84: II-299 (abstract), *Clin Ther* 1993; 15:374–382, *Jpn Heart J* 1996; 37:327–32, *Am Heart J* 1996; 132:23–29, *J Am Coll Cardiol* 1997; 30:855–62). Recently, we have shown in the MultiVitamins and Probucol (MVP) randomized clinical trial that probucol, a drug with strong antioxidant properties, given alone reduced angiographic lumen loss by 68%, restenosis rate per segment by 47% and the need for repeat angioplasty at 6 month by 58% compare to placebo. These results have been recently published (Multivitamins and probucol in the prevention of restenosis after coronary angioplasty: Results of the MVP randomized trial. *N Engl J Med* 1997; 365–372) and the publication is incorporated herein by reference. It was not possible to determine with angiography alone whether probucol acted via inhibition of tissue hyperplasia or improvement in vascular remodeling. Determination of this mechanistic question was necessary to help identify the appropriate targets in the periangioplasty period and, as taught by the present invention, lead to more effective strategies to prevent restenosis. In addition, the invention enables the skilled practitioner to use probucol in conjunction with other percutaneous coronary interventions such as stenting if it is deemed appropriate.

We have performed serial intravascular ultrasound (IVUS) examinations in a consecutive series of patients involved in the MVP trial. By providing tomographic views of coronary arteries with high resolution, IVUS allows quantitative assessment of changes in arterial lumen and wall dimensions. We were therefore able in this study to determine the pathophysiology of coronary restenosis after balloon angioplasty in patients systematically undergoing follow-up IVUS examination and determine the effect of probucol on tissue hyperplasia and vascular remodeling after coronary angioplasty.

BRIEF DESCRIPTION OF THE DRAWINGS

The present invention will be further understood with reference to the drawings, wherein.

DETAILED DESCRIPTION OF THE INVENTION

Study Design and Population

The present invention concerns the IVUS substudy from the MVP restenosis trial. MVP was a double-blind placebo-controlled randomized clinical trial with four study groups. The protocol was approved by the Montreal Heart Institute institutional review board. The MVP study design, inclusion and exclusion criteria have been previously described (*N Engl J Med* 1997; 365–372). Briefly, patients referred for elective coronary angioplasty were evaluated at least 30 days prior to their scheduled procedure. Eligible patients were asked to provide written informed consent. Patients were eligible if they were scheduled to undergo standard balloon angioplasty on at least 1 native coronary artery and had at least 1 de novo target lesion with luminal narrowing of 50% or more by caliper measurements.

Beginning 30 days prior to scheduled angioplasty, patients were randomly assigned to receive either probucol alone, multivitamins alone, the combination of probucol and multivitamins, or placebo. Probucol 500 mg or matched placebo was administered twice daily. The multivitamin complex, consisting of vitamin E 700 IU, vitamin C 500 mg and beta-carotene 30,000 IU, or matched placebo was also administered in one tablet twice daily. All patients received an extra dose of probucol 1000 mg and/or vitamin E 2000 IU and/or matched placebos 12 hours before angioplasty, according to randomization assignment. After angioplasty, all successfully dilated patients who did not present a periprocedural complication were maintained on their assigned study regimen until follow-up angiography was performed. All patients received aspirin 325 mg daily started at least 30 days before procedure and continued for the study period. Balloon angioplasty was performed according to standard techniques. Intracoronary nitroglycerin (0.3 mg) was given for each target artery for both pre- and post-dilatation angiography and at follow-up. The sequence of contrast injections with the exact degree of angulation was recorded and used for every angiogram. Coronary arteriograms (pre-, post-procedure, and final follow-up) were analyzed together using the Coronary Measurement System (CMS), as we have previously reported. Patient follow-up included clinical evaluation, exercise treadmill testing, blood chemistry, pill count and drug level measurements, and dietary assessment and intervention. Patients were readmitted for follow-up coronary angiography at 5 to 7 months. Patients in whom arteriography was performed for clinical reasons before the fifth month returned for repeat angiographic examination at 5 to 7 months if no definite angiographic restenosis was present on at least 1 dilated site. During follow-up, patients with recurrence or exacerbation of anginal symptoms were treated with medical therapy or revascularization procedures (reangioplasty or Coronary Bypass Surgery) as clinically indicated. Patients with angiographic restenosis (lesion>50%. at follow-up) without clinical evidence of ischemia were not subjected to further interventional procedures.

The MVP study was stopped prematurely by an independent monitoring board after 317 patients had entered the trial because one treatment had a significant effect on the primary (angiographic) efficacy endpoint. 111 patients underwent IVUS examination of the angioplasty site after final balloon inflation at baseline and constituted the initial population for the IVUS study.

IVUS Instrumentation and Examination

IVUS examinations were performed using 30 MHZ, 3.5 French mechanical (1800 rpm) ultrasound catheters (Boston Scientific, Natick, Mass.) and a dedicated imaging console (Hewlett Packard, Andover, Mass.) (*Curr Opin Cardiol* 1994; 9:627–633). In six patients, both examinations were performed using 20 MHZ, 3.5 French 64-element IVUS catheters (Endosonics, Pleasanton, Calif.). IVUS studies were first performed after coronary angioplasty (after final balloon inflation) and then after follow-up angiography (before any subsequent intervention) and were always preceded by administration of intracoronary nitroglycerin (0.3 mg). IVUS imaging was monitored by an experienced cardiologist, but the angioplasty operator was blinded to ultrasound results to avoid altering standard balloon angioplasty practice. The IVUS catheter was advanced distal to the dilated site to an easily recognizable landmark, most often a side branch, which was noted and used for follow-up IVUS examination. One angiographic view was recorded on videotape before beginning pullback of the IVUS catheter. Slow manual pullbacks (approximately 0.5 mm/sec) were performed up to the guiding catheter and the ultrasound images recorded onto 0.5 inch S-VHS videotape for off-line analysis, with a detailed running audio commentary describing the location of the ongoing IVUS interrogation including the angioplasty site. Simultaneous high-resolution fluoroscopic images were recorded on the IVUS imaging screen during pullbacks to constantly know the location of the IVUS transducer. The operator was allowed to pause at sites of interest (e.g., angioplasty site, side branches) and contrast injections were performed when necessary to identify major and selected minor side branches, to accurately define the position of the IVUS catheter in relation to the angioplasty site and to improve delineation of the lumen-intima interface. Gain settings were carefully optimized during the initial assessment and changed only if required due to suboptimal image quality.

Quantitative IVUS Measurements

Figure 1:
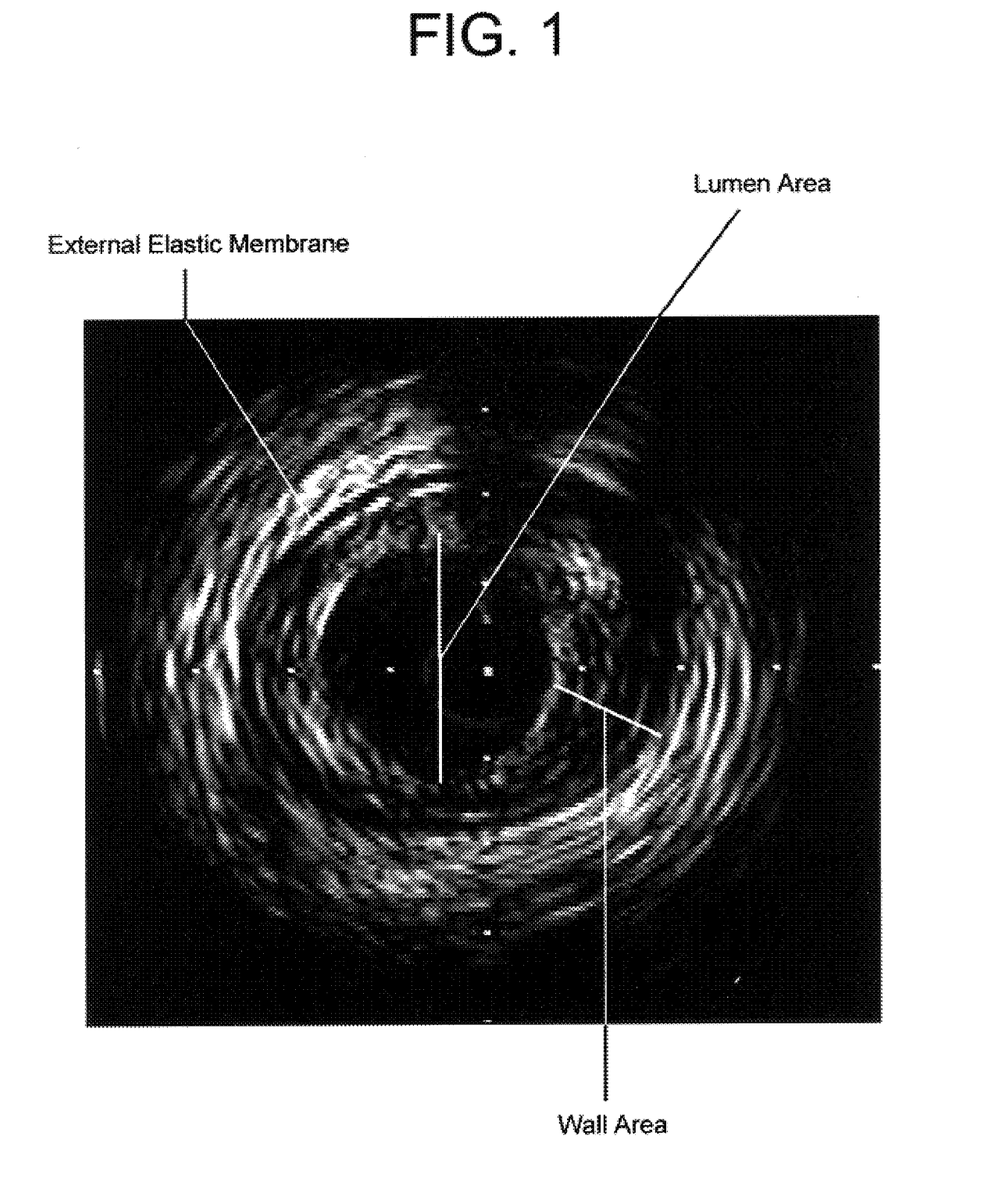
FIG. 1 shows a tomographic section of a coronary artery (single frame of an IVUS study). The lumen area, the wall or plaque area and the external elastic membrane are identified.

All the IVUS images were interpreted by experienced technicians supervised by a cardiologist blinded to treatment assignment. The post-angioplasty and follow-up studies were analyzed side by side. Great care was taken to ensure that the same and correct anatomic slice was measured in both IVUS studies. The fluoroscopic and angiographic images and audio commentary were used to determine the axial location of the ultrasound transducer and of IVUS landmarks relative to the angioplasty site and to side branches. IVUS landmarks (side branches, veins, calcifications, fibrotic deposits) were used to allow matching of the anatomic slice in both studies using frame by frame review of the images. The anatomic cross-section selected for serial analysis was the one at the angioplasty site with the smallest lumen area at follow-up. The corresponding anatomic slice was then identified on the post-angioplasty study. The images were digitized and quantitative analysis performed using custom-developed software for geometric computations (NIH Image 1.59). Quantitative analysis consisted in measurements of lumen area and the area within the external elastic membrane (EEM) (FIG. 1). The external elastic membrane was defined as the border between the hypoechoic media zone and the surrounding echobright adventitia. Wall area was calculated as the difference between EEM and lumen areas. When the plaque encompassed the IVUS catheter, the lumen area was assumed to be the size of the catheter.

Measurement of the EEM area can be difficult in the presence of extensive calcifications, because of acoustic shadowing of deeper structures. Two strategies were used to circumvent this problem (*J Am Coll Cardiol* 1997; 29:268–274). Considering that coronary arterial cross-sections are relatively circular, extrapolation of the EEM level was directly performed when each arc of calcification at the selected site did not shadow more than 60 degrees of the adventitial circumference. In addition, study of the anatomic slices just proximal and just distal to a selected calcified site was also performed when necessary to escape the shadowing and to identify the EEM correctly.

Statistical Methods

Statistical analysis was performed for all patients who underwent both baseline and follow-up examinations. The same analyses were performed for compliant patients only (efficacy analysis). Measurements are reported as mean±1 SD. The relations between changes in lumen, wall and EEM areas within study groups were tested using least squares linear regression analyses and Pearson's correlation coefficients. IVUS measurements were analyzed between groups with a two-way analysis of covariance (Fleiss JL. The design and analysis of clinical experiments. New York: John Wiley and Sons, 1986; 186–194) on follow-up areas, controlling for post-angioplasty area and for potential prognostic factors and extracting treatment effects and interactions. The IVUS measurements were analyzed per segment by the generalized estimating equations (GEE) technique (*Biometrika* 1986; 73:13–22), which takes into account potential dependence between segments in the same patient.

Results

Of the 107 patients who underwent IVUS examination of the angioplasty site immediately after intervention, 11 were not studied at follow-up for different reasons. Two patients underwent both IVUS studies but extensive calcifications precluded quantitative IVUS measurements at the selected angioplasty site. Thus, 94 patients constituted our study population and were distributed in the four groups as follows: 21 received probucol alone, 25 multivitamins alone, 20 probucol plus multivitamins and 28 received only placebo. Selected demographic, clinical and angiographic characteristics of the four groups are shown in Table 1. There were no statistically significant baseline differences between study groups. Six patients were not adequately compliant to study medications (1, 2, 2 and 1 in the probucol, vitamins, combined treatment and placebo groups). There were also no baseline differences between groups when compliant patients only were evaluated.

Natural History of Restenosis: IVUS Results in the Placebo Group

Table 2 summarizes IVUS results for the placebo alone group and for the 3 active treatment groups. At baseline (immediately after angioplasty) in the placebo group, lumen, wall and EEM areas were 4.52±1.39 $mm^2$, 8.85±3.01 $mm^2$, and 13.37±3.45 $mm^2$, respectively. At follow-up, these values were 3.31±1.44 $mm^2$, 10.35±3.95 $mm^2$, and 13.66±4.18 $mm^2$. Thus, lumen area at follow-up decreased by −1.21±1.88 mm², and wall and EEM areas increased by 1.50±2.50 mm² and 0.29±2.93 mm². The change in lumen area correlated more strongly with the change in EEM area r=0.53, p=0.002) than with the change in wall area r=−0.13, p=0.49).

Figure 2:
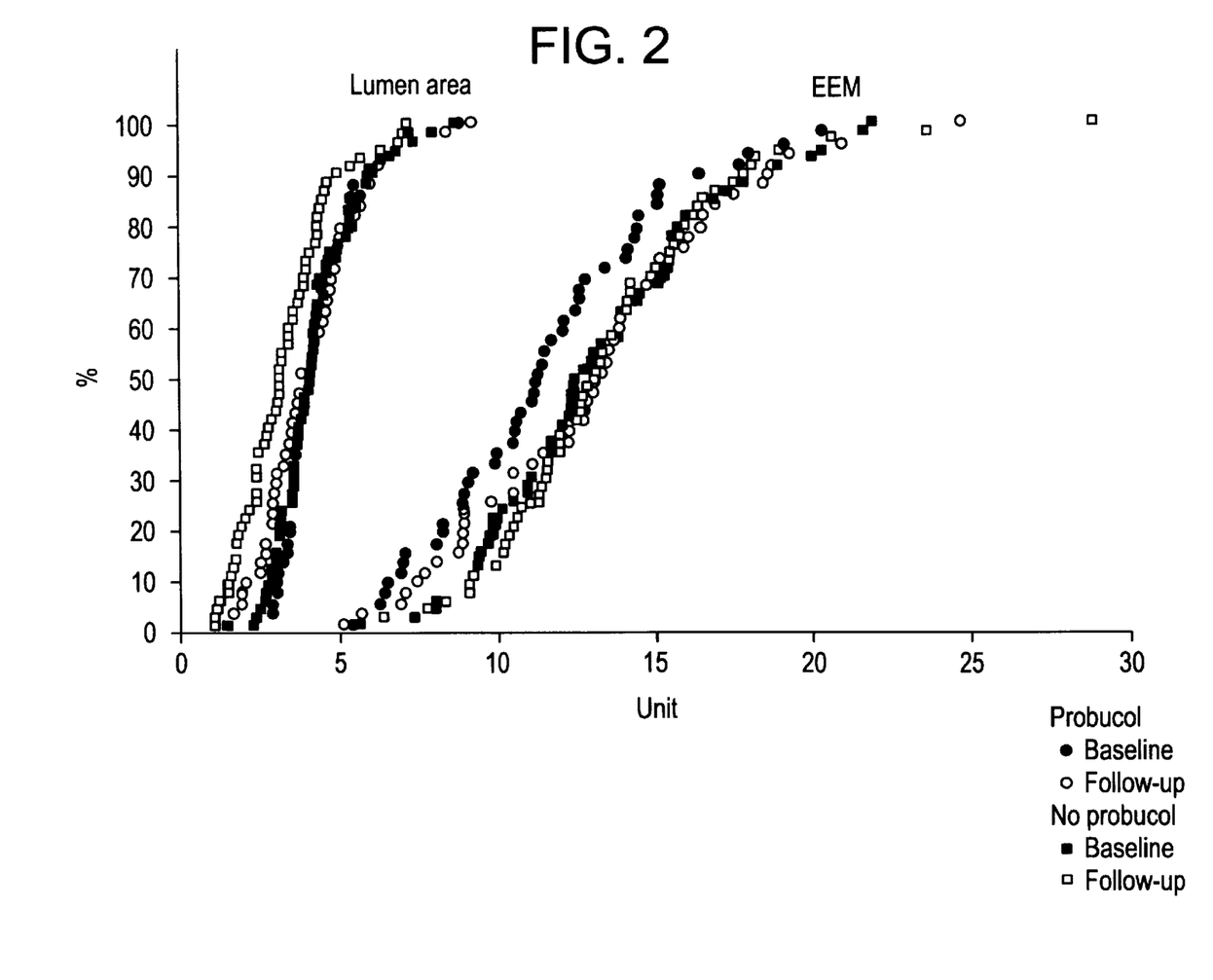
FIG. 2 represents the cumulative frequency curves of the lumen and EEM areas observed by IVUS in all study groups.

Effects of Probucol and Vitamins on Tissue Hyperplasia and Vascular Remodeling: IVUS Results in the Four Study Groups Lumen area at follow-up was 3.31±1.44 mm² in the placebo group, 3.24±1.58 mm² for vitamins only, 3.85±1.39 mm² for combined treatment and 4.47±1.93 mm² for probucol alone (p=0.002 for probucol versus no probucol; p=0.84 for vitamins versus no vitamins). Follow-up wall area was 10.35±3.95 mm² for the placebo group, 10.02±3.40 mm² in the vitamins only group, 8.52±3.49 mm² for combined treatment and 9.46±4.36 mm² for probucol alone (p=0.27 for probucol versus no probucol and 0.18 for vitamins versus no vitamins). EEM area at follow-up was 13.66±4.18 mm² in patients receiving placebo alone, 13.26±3.80 mm² for vitamins only, 12.37±3.70 mm² for combined treatment and 13.93±4.74 mm² for those treated with probucol only (p=0.005 for probucol versus no probucol; p=0.36 for vitamins versus no vitamins). FIG. 2 represents the cumulative frequency curves of the lumen and EEM areas observed on IVUS in all study groups.

Figure 3:
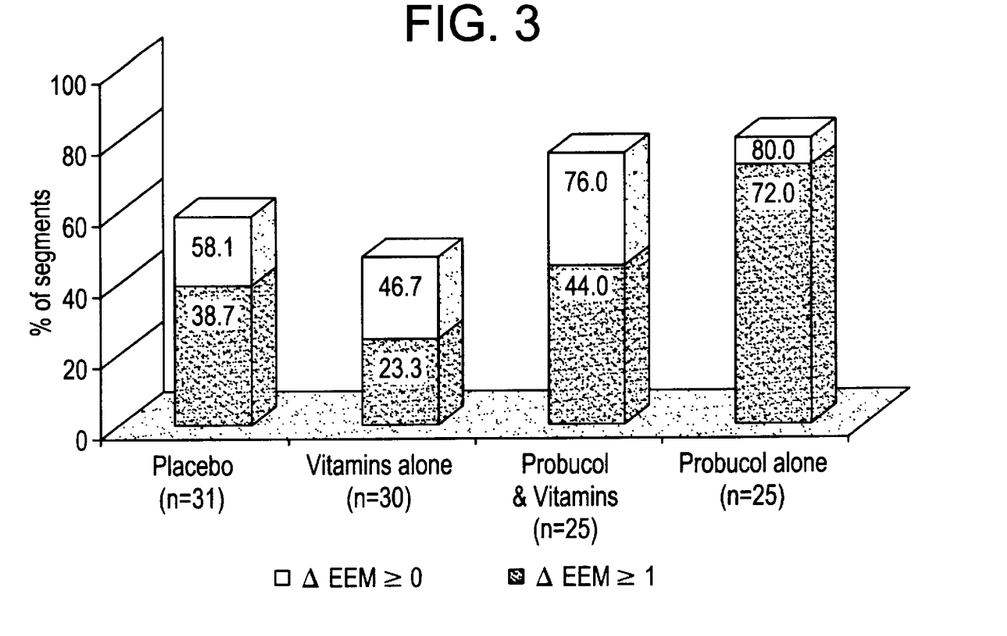
FIG. 3 shows the proportion of segments for each treatment group showing an increase in the external elastic membrane surface area between baseline and follow-up. Lower bars depict the proportion of segments showing a growth greater or equal to 1 $mm^2$.

Lumen loss was 1.21±1.88 mm² in the placebo group, 0.83±1.22 mm² for vitamins alone, 0.25±1.17 mm² for combined treatment and 0.15±1.70 mm² for patients receiving probucol alone (p=0.002 for probucol versus no probucol and p=0.84 for vitamins versus no vitamins). The change in wall area was 1.50±2.50 mm², 0.93±2.26 mm², 1.41±1.45 mm² and 1.89±1.87 mm₂, respectively (p=NS). EEM area increased at follow-up by 0.29±2.93 mm² in the placebo group, 0.09±2.33 mm₂ in the vitamins only group, 1.17±1.61 mm² for combined treatment and 1.74±1.80 mm² for the probucol alone group (p=0.005 for probucol versus no probucol and p=0.36 for vitamins versus no vitamins). An increase in EEM area of at least 1 mm² at follow-up occurred in 38.7% of patients given placebo alone, in 23.3% in the vitamins only group, 44.0% in the combined treatment group, and 72.0% of patients taking probucol (FIG. 3). Table 3 shows the changes in lumen, wall and EEM areas for compliant patients only.

TABLE 1

BASELINE DEMOGRAPHIC, CLINICAL AND ANGIOGRAPHIC CHARACTERISTICS OF THE FOUR STUDY GROUPS

|  | Placebo Alone | Vitamins Alone | Probucol + Vitamins | Probucol Alone |
|---|---|---|---|---|
| Patients | 28 | 25 | 20 | 21 |
| Age (yrs) (means ± SD) | 59.5 ± 8.8 | 58.1 ± 11.1 | 57.1 ± 8.9 | 56.1 ± 7.8 |
| Female (%) | 28.6 | 8.0 | 30.0 | 9.5 |
| Ever Smoked (%) | 17.9 | 8.0 | 25.0 | 4.8 |
| Current Smoker (%) | 7.1 | 28.0 | 15.0 | 19.1 |
| Hist. of | 7.1 | 0 | 20.0 | 20.0 |
| Diabetes (%) |  |  |  |  |
| Hist. of Hypertension (%) | 42.9 | 52.0 | 50.0 | 14.3 |
| CCS angenia class (%) |  |  |  |  |
| I | 0 | 4.0 | 10.0 | 14.3 |
| II | 53.6 | 56.0 | 65.0 | 66.7 |
| III | 28.6 | 24.0 | 10.0 | 14.3 |
| IV | 0 | 0 | 0 | 0 |
| Prior MI (%) | 32.1 | 52.0 | 50.0 | 52.4 |
| Prior CABG (%) | 7.1 | 0 | 5.0 | 0 |
| Prior PTCA (%) | 7.1 | 8.0 | 15.0 | 4.8 |
| No. of Diseased Vessels (%) |  |  |  |  |
| 1 | 39.3 | 36.0 | 45.0 | 33.3 |
| 2 | 39.3 | 48.0 | 25.0 | 42.9 |
| 3 | 21.4 | 16.0 | 30.0 | 23.8 |
| Target Vessels (%) |  |  |  |  |
| Left anterior descending | 54.8 | 56.7 | 33.0 | 40.0 |
| Left circumflex | 16.1 | 20.0 | 24.0 | 36.0 |
| Right coronary artery | 29.0 | 23.3 | 32.0 | 24.0 |
| Maximum pressure (mean ± SD) | 10.8 ± 2.2 | 10.8 ± 3.2 | 10.3 ± 2.7 | 10.1 ± 2.1 |
| Total Inflation Time (sec) | 513 ± 236 | 496 ± 205 | 438 ± 209 | 516 ± 277 |
| Balloon to Artery Ratio | 1.04 ± 0.17 | 1.02 ± 0.10 | 1.06 ± 0.22 | 1.09 ± 0.11 |

CABG: Coronary artery bypass graft

MI: Myocardial infraction

PTCA: Percutaneous transluminal coronary angioplasty

*p = 0.042 based on Chi-squared test

TABLE 2

SERIAL INTRAVASCULAR ULTRASOUND RESULTS*

|  | Placebo Alone (n = 31) | Vitamin Alone (n = 30) | Probucol & Vitamins (n = 25) | Probucol Alone (n = 25) | p value Probucol vs. No Probucol | p Value Vitamins vs. No Vitamins |
|---|---|---|---|---|---|---|
| After Angioplasty |  |  |  |  |  |  |
| Lumen area (mm$^2$) | 4.52 ± 1.39 | 4.08 ± 1.41 | 4.10 ± 0.95 | 4.62 ± 1.59 | 0.7885 | 0.0544 |
| EEM area (mm$^2$) | 13.37 ± 3.45 | 13.17 ± 3.90 | 11.21 ± 3.25 | 12.20 ± 4.66 | 0.0261 | 0.4258 |
| Wall area (mm$^2$) | 8.85 ± 3.01 | 9.09 ± 3.28 | 7.11 ± 2.75 | 7.57 ± 3.98 | 0.0071 | 0.8930 |
| Follow-up |  |  |  |  |  |  |
| Lumen area (mm$^2$) | 3.31 ± 1.44 | 3.24 ± 1.58 | 3.85 ± 1.39 | 4.47 ± 1.93 | 0.0022 | 0.8449 |
| EEM area (mm$^2$) | 13.66 ± 4.18 | 13.26 ± 3.80 | 12.37 ± 3.70 | 13.93 ± 4.74 | 0.0055 | 0.3590 |
| Wall area (mm$^2$) | 10.35 ± 3.95 | 10.02 ± 3.40 | 8.52 ± 3.49 | 9.46 ± 4.36 | 0.2739 | 0.1795 |
| Follow-up-Post PTCA |  |  |  |  |  |  |
| Lumen area (mm$^2$) | −1.21 ± 1.88 | −0.83 ± 1.22 | −0.25 ± 1.17 | −0.15 ± 1.70 | 0.0022 | 0.8449 |
| EEM area (mm$^2$) | 0.29 ± 2.93 | 0.09 ± 2.33 | 1.17 ± 1.61 | 1.74 ± 1.80 | 0.0055 | 0.3590 |
| Wall area (mm$^2$) | 1.50 ± 2.50 | 0.93 ± 2.26 | 1.41 ± 1.45 | 1.89 ± 1.87 | 0.2739 | 0.1795 |

*Per segment analysis using the GEE technique

TABLE 3

EFFICACY ANALYSIS IN COMPLIANT PATIENT

|  | Placebo Alone (n = 30) | Vitamins Alone (n = 28) | Probucol & Vitamins (n = 23) | Probucol Alone (n = 25) | p value Probucol vs. No Probucol | p Value Vitamins vs. No Vitamins |
|---|---|---|---|---|---|---|
| Follow-up-Post PTCA |  |  |  |  |  |  |
| Δ Lumen area (mm$^2$) | −1.04 ± 1.67 | −0.78 ± 1.25 | −0.25 ± 1.20 | −0.07 ± 1.69 | 0.0020 | 0.5605 |
| Δ EEM area (mm$^2$) | 0.48 ± 2.77 | 0.10 ± 2.23 | 1.15 ± 1.60 | 1.88 ± 1.69 | 0.0034 | 0.1989 |
| Δ Wall area (mm$^2$) | 1.52 ± 2.54 | 0.89 ± 2.15 | 1.40 ± 1.31 | 1.95 ± 1.88 | 0.2179 | 0.1345 |

There was no statistically significant drug interaction in the factorial design. However, considering potential underpowering to detect such an interaction, post-hoc analyses comparing each group separately and adjusted for a possible interaction were performed. Results remained significant for all ultrasound endpoints between the probucol alone and placebo groups.

Probucol is one of the first pharmacological interventions shown to prevent coronary restenosis after balloon angioplasty. However, its mechanism of action and its efficacy as a vascular remodeling agent has never been studied. In the MVP study, probucol therapy initiated 30 days before and given alone for 6 months after angioplasty resulted in reductions, of 68% in angiographic lumen loss, 47% in restenosis rate per segment and 58% in the need for repeat angioplasty when compared to placebo. Whether probucol acted via prevention of tissue hyperplasia, improvement in vascular remodeling, or both, could not be adequately addressed by angiography and required the use of IVUS. It was necessary to determine the mechanism of action of probucol in order to develop better strategies against restenosis. These strategies are unequivocally needed. Indeed, although probucol drastically reduced angiographic lumen loss in the MVP study, restenosis still occurred in over 20% of patients given probucol alone. Furthermore, the positive results found with stents have predominantly been obtained in patients with large coronary arteries, i.e., 3.0 mm in diameter or more (*N Engl J Med* 1994; 331:489–495, *N Engl J Med* 1994; 331:496–5). In a subset analysis of patients randomized in the BENESTENT trial and having interventions performed on small vessels (<3.0 mm), the benefits noted in the patients with larger vessels (>3.0 mm) were not seen (*Semin Intervent Cardiol* 1996; 1:255–262). In the stented population, smaller vessel size was associated with a higher stent/vessel ratio, a greater relative gain and a greater subsequent loss index, and a higher risk of adverse cardiac events within six months of the procedure.

Before learning how probucol acted in the MVP study, it was first necessary to clarify the mechanisms of lumen loss and restenosis after balloon angioplasty in the placebo group. In these control patients, the increase in wall area (mean: 1.50 mm$^2$) was greater than the decrease in lumen area (−1.21 mm$^2$) with a slight increase of the EEM area (0.29 mm$^2$). However, the change in lumen area correlated better with the change in EEM area than with the change in wall area. Taken together, these results indicate that the direction (enlargement [positive] or constriction [negative]) and extent (e.g., inadequate or adequate compensatory enlargement) of vascular remodeling in response to the tissue hyperplasia that occurs after balloon angioplasty determine the magnitude of lumen loss at follow-up. Animal studies have yielded various results on the relative importance of remodeling and tissue hyperplasia in the pathogenesis of restenosis. Animal models, however, have different proliferative and thrombogenic responses to arterial trauma, and plaque content is often significantly different than what is found in human atherosclerotic stenoses requiring angioplasty. One additional limitation is that wall and EEM (or internal elastic lamina) areas were never measured serially with the same method in a given animal artery.

Although clinical studies have revealed that remodeling occurs in humans after different interventions, relative changes in wall and EEM areas have varied. Mintz, et al. observed that 73% of late lumen loss after intervention was explained by a decrease in EEM area (Circulation 1996; 94:35–43). As acknowledged by the authors, however, the study involved a mix of primary and restenotic lesions on which different interventions were performed. Balloon angioplasty was performed alone in only a small minority of patients, and follow-up examination was largely driven by the presence of symptoms. An underestimation of the increase in plaque area may also have occurred because of the larger acoustic size (i.e., physical catheter size+central artifact) of the catheters that were used in that study. Preliminary data from the SURE study now appear to show that most of the lumen loss from immediately after to six months after balloon angioplasty ($-1.51$ mm$^2$) was not caused by a decrease in EEM area ($-0.46$ mm$^2$) (J Am Coll Cardiol 1996; 27:41A).

Whereas data from this and other studies support the conclusion that lumen loss after balloon angioplasty is caused by the combination of inadequate or deleterious vessel remodeling and tissue hyperplasia, probucol in the MVP study significantly reduced lumen loss by improving vascular remodeling but it did not modify the post-angioplasty increase in wall area. When compared to non-probucol treated patients, those receiving probucol showed a reduction in lumen loss by 80% or 0.79 mm$^2$ when assessed by IVUS. When compared to the placebo group only, the reduction in lumen loss with probucol given alone was 88% or 1.06 mm$^2$. A striking improvement in compensatory vessel enlargement was responsible for probucol's favorable effect on lumen loss. There was an enlargement in EEM area of 1.74 mm$^2$ from immediately after angioplasty to follow-up in patients treated with probucol alone compared with 0.29 mm$^2$ in patients given placebo. This represents a 730% increase in vessel enlargement in patients given probucol only. Five other clinical studies, smaller than MVP, have also observed the antirestenotic effect of probucol using angiography (Circulation 1991; 84:II-299 (abstract), Clin Ther 1993; 15:374–382, Jpn Heart J 1996; 37:327–32, Am Heart J 1996; 132:23–29, J Am Coll Cardiol 1997; 30:855–62). In addition, a better arterial response after balloon injury has been demonstrated with probucol in animal studies (Circulation 1993; 88:628–637, Proc Natl Acad Sci 1992; 89:11312–11316). Other antioxidants were also specifically shown in animals to improve vascular remodeling after angioplasty (Arterioscle Thromb Vasc Biol 1995; 15:156–165). Thus, results from the MVP trial and from these other studies provide strong support for the central role of oxidative processes in the pathophysiology of restenosis Oxygen free radicals generated by damaged endothelium, activated platelets and neutrophils at the angioplasty site (Mayo Clin Proc 1988; 63:381–389) can induce chain reactions which result in endothelial dysfunction (Nature 1990; 344:160–162) and LDL oxidation (N Engl J Med 1989; 320:915–924). Macrophages activated by oxidized LDL and dysfunctional endothelium can then release several cytokines and growth factors promoting matrix remodeling and smooth muscle cell proliferation. Matrix degradation by metalloproteinases precedes or accompanies early formation of new extracellular matrix (Circ Res 1994; 75:650–658) after angioplasty and also is a crucial step before smooth muscle cell migration and proliferation (Circ Res 1994; 75:539–545, Biochem J 1992; 288:93–99). Interestingly, it has recently been shown that oxygen free radicals can modulate matrix remodeling by activating metalloproteinases (J Clin Invest 1996; 98:2572–2579). The same events that lead to an increase in wall area after angioplasty, i.e., matrix formation and smooth muscle cell proliferation, are likely involved in the process of vascular remodeling. Smooth muscle cell contraction (Crit Care Med 1988; 16:899–908), along with cross-linking of collagen fibers (J Am Coll Cardiol 1995; 25:516–520), may limit compensatory vessel enlargement in response to tissue hyperplasia and may even result in vascular constriction. Again, nonenzymatic cross-linking of collagen typically involves oxidation processes (FASEB J 1992; 6:2439–2449). In addition, chronic flow-dependent changes in vessel size may be limited by endothelial dysfunction (Science 1986; 231:405–407).

Not being bound by any theory, the powerful chain-breaking antioxidant effects of probucol (Am J Cardiol 1986; 57:16H-21) may have prevented endothelial dysfunction (J Lipid Res 1991; 32:197–204, N Engl J Med 1995; 332:488–493), LDL oxidation (J Clin Invest 1986; 77:641–644) and macrophage and metalloproteinase activation in the MVP study. This could have limited smooth muscle cell activation, migration, proliferation and contraction, and matrix degradation and deposition of new collagen and other fibers. By ultimately limiting smooth muscle cell contraction, collagen formation and cross-linking, and endothelial dysfunction through its antioxidant effects, probucol can modify vascular remodeling and allow greater vessel enlargement. The hypocholesterolemic effect of probucol is weak and unlikely by itself to be responsible for the positive MVP results. However, specific inhibition by probucol of secretion of interleukin-1 (Am J Cardiol 1988; 62:77B-81B) may have decreased secretion of metalloproteinases (Circ Res 1994; 75:181–189) and modified matrix remodeling.

Figure 4:
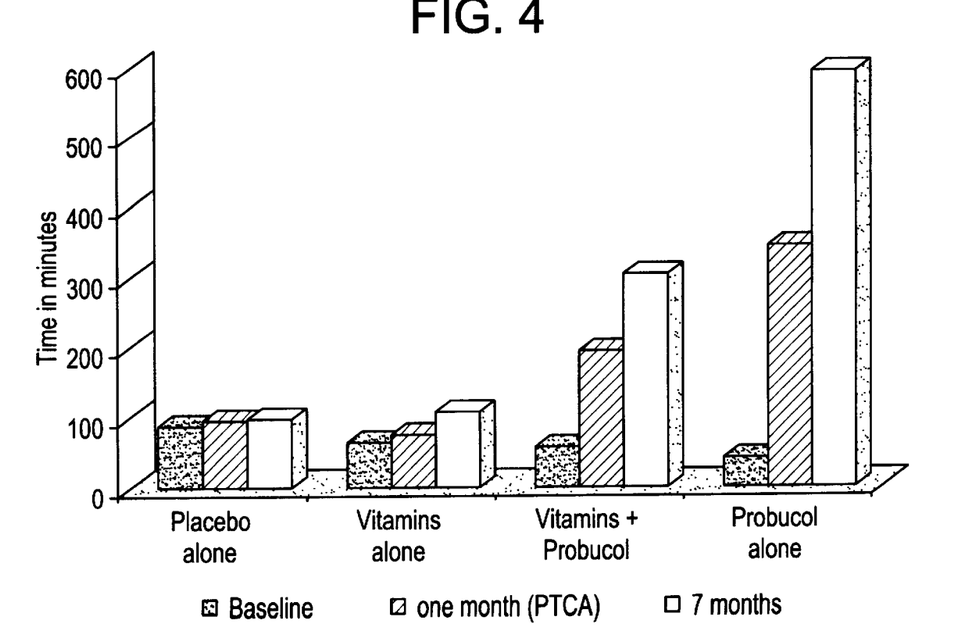
FIG. 4 shows the lag phase for LDL peroxidation for all four treatment groups at baseline, 1 month and 7 months post-treatment initiation

Similar to what we observed clinically and angiographically, multivitamins had no significant effect on IVUS endpoints. It is not clear why multivitamins did not prevent restenosis whereas probucol did. Dietary intervention and smoking habits were similar in all groups. Probucol may simply be a more powerful antioxidant than the combination of vitamins. To this regard, preliminary results from the continuous spectrophotometric monitoring of diene conjugates in LDL after the addition of copper ions to the isolated lipoprotein ex vivo (Free Radic Res Commun 1989; 6:67–75) of MVP patients are noteworthy. FIG. 4 shows the lag phase for LDL peroxidation for all four treatment groups at baseline, one month and seven months post-treatment initiation. Although LDL trapped in the arterial intima encounters a very complex environment, compared with the simple set-up of oxidation resistance assays, our results would suggest that probucol treatment for one month provided a significantly greater protection against LDL oxidation than vitamins alone or the combination of probucol and vitamins. Although the described (Science 1984; 224:569–73) pro-oxidant effects of high doses of multivitamin was not evident ex vivo in the vitamins alone group, it does not exclude the possibility that it may have played a role in vivo. Alternatively, the effect of probucol on interleukin-1 and on reverse cholesterol transfer may have contributed to this result.

Lumen loss after balloon angioplasty is shown to be due to inadequate vessel remodeling in response to tissue hyperplasia. We have shown using IVUS that probucol exerts its antirestenotic effects in humans by improving vascular remodeling after angioplasty. The disclosure describes the positive vascular remodeling effects of probucol using the balloon angioplasty procedure as an example. Probucol, the first pharmacologic agent demonstrated to have positive vascular remodeling capabilities, or any other similar agent to be described in the future for that matter, would be useful in a variety of clinical conditions associated with arterial wall injury. Such conditions could be of natural origin or iatrogenic. More specifically, natural conditions may include hypertensive disorders, vascular disorders affecting the coronaries, the peripheral arteries, the cerebral arteries, the pulmonary arteries, the vascular supply to the kidneys, and any other organ in the abdominal cavity, etc. Iatrogenic conditions for which probucol or a positive vascular remodeling agent may be beneficial could include conditions such as post-coronary intervention, i.e., balloon angioplasty, directional or rotational atherectomy, laser-assisted angioplasty, post-radiation therapy, or coronary stenting or any other intervention which may be associated with vascular injury which will lead to intimal proliferation or negative vascular remodeling (constriction). The potential benefit of a positive vascular remodeling agent would not be limited to the coronary tree. Similar vascular injury in the renal, carotid, vertebral, mesenteric, peripheral vascular bed would also benefit from such an agent. In other conditions, such as post-bypass surgery, the conduit utilized for bypass (vein or artery) would also benefit from a vascular remodeling agent. Such an agent could favor the development (growth) of the graft immediately post-surgery and/or prevent its occlusion due to intimal hyperplasia or atherosclerotic process. Patients with renal failure treated with hemodialysis through an arteriovenous fistula frequently show intimal proliferation and progressive disease of their shunt, which eventually will occlude. Vascular remodeling agent may be beneficial and prolong the life of the shunt. Post-organ transplant, vascular damage and intimal proliferation, which may lead to vascular obstruction and graft damage, is a frequent problem that may also benefit from the use of a vascular remodeling agent. In addition, vascular remodeling agent could play a role in the treatment of patients with a condition such as primary pulmonary hypertension.

So far, the invention and its applications have only been described for the vascular system. It is intended to encompass with these claims the use of such an agent for any condition where a structure surrounded by a muscular wall will benefit from having its wall remodeled (expansion) so doing creating a larger conduit or cavity.

Probucol or the agent with positive vascular remodeling properties could be administered systemically or locally. Systemic administration may be accomplished with intravenous/intra-arterial injection (bolus injection or longer perfusion) orally (any forms of oral delivery systems), subcutaneously (injection, pallet, slow release, etc.), percutaneously (patch, cream, gel, etc.) with short-acting or long-acting (slow release) delivery profile. A local delivery system would include any device intended to locally deliver probucol or a similar agent (i.e., local delivery catheter, coated or impregnated stent, local infusion device, etc.).

Further variations and modifications will be apparent to those skilled in the art and are intended to be encompassed by the claims appended hereto.

What is claimed is:

1. A method of preventing or treating hyperproliferative vascular disease through vascular remodeling in a susceptible mammal, comprising:
   administering to said mammal, in need thereof, an amount of probucol, or a pharmaceutically acceptable salt thereof, effective in compensating for smooth muscle proliferation and intimal thickening by promoting positive vascular remodeling in said mammal.

2. The method of claim 1, wherein the drug delivery is accomplished by oral, parenteral, intravascular, intromuscular, intranasal, intrabronchial, transdermal, rectal administration, or via local delivery of the drug with a local delivery system (passive or active) or with a drug impregnated vascular stent or other device slowly delivering the drug locally.

3. The method of claim 1, wherein the probucol or a pharmaceutically acceptable salt thereof is administered prior to and/or concurrent with said mammal undergoing a percutaneous transluminal coronary angioplasty procedure.

4. The method of claim 3, which further comprises administering the probucol or a pharmaceutically acceptable salt thereof subsequent to said mammal undergoing a percutaneous transluminal coronary angioplasty procedure.

5. The method of claim 1, wherein the hyperproliferative vascular disease is selected from the group consisting of intimal smooth muscle cell hyperplasia, restenosis, atherosclerotic plaque and vascular occlusion secondary to other mechanisms.

6. The method of claim 5, wherein the hyperproliferative vascular disease is restenosis.

7. The method of claim 1, wherein the probucol or a pharmaceutically acceptable salt thereof is administered prior to, concurrent with and/or subsequent to said mammal undergoing a procedure which is a member selected from the group consisting of transluminal angioplasty, ballon angioplasty, directional atherectomy, rotational atherectomy, laser-assisted angioplasty, post-radiation therapy, coronary stenting, bypass surgery and organ transplant.

8. The method of claim 1, wherein the probucol or a pharmaceutically acceptable salt thereof, is administered prior to, concurrent with and/or subsequent to said mammal sustaining a biologically mediated vascular injury.

9. The method of claim 1, wherein the probucol or a pharmaceutically acceptable salt thereof is administered prior to, concurrent with and/or subsequent to said mammal sustaining a mechanically mediated vascular injury.

10. A sustained release device for releasing probucol to improve vascular remodeling comprising:

probucol or a pharmaceutically acceptable salt thereof in a form that is consistently and progressively released from a device over a certain period of time when implanted in or near a blood vessel.

11. The sustained release device of claim 10, wherein the device is in the form of a stent.

12. A local delivery device for releasing probucol to promote vascular remodeling comprising:

probucol or a pharmaceutically acceptable salt thereof in a form that is released from a device when temporarily positioned or permanently implanted in or near a blood vessel.

13. The local delivery device of claim 12, wherein the device is in the form of a local delivery or infusion catheter, a coated or impregnated stent or any other endovascular device allowing local infusion.

14. The method of claim 1, wherein the probucol or a pharmaceutically acceptable salt thereof is administered for treatment of a injury to a vasculature selected from the group consisting of the coronary tree, carotid artery, vertebral artery, iliac artery, femoral artery, renal artery, the thoracic and abdominal aorta and its branches, mesenteric, pulmonary, and peripheral vascular bed.

15. A method of treatment for the expansion of a muscular wall of a mammal, comprising:

administering to said mammal in need thereof muscular wall expansion an effective amount of probucol, or a pharmaceutically acceptable salt thereof.

16. The method of claim 1 wherein the positive vascular remodeling is treatment for a condition selected from the group consisting of high blood pressure, pulmonary hypertension, post-organ transplant, progressive disease of an arterio-venous shunt and cardiac bypass surgery.

* * * * *